United States Patent [19]

Rai et al.

[11] Patent Number: 4,986,909

[45] Date of Patent: * Jan. 22, 1991

[54] CHROMATOGRAPHY COLUMN

[75] Inventors: Vish Rai, Wallingford; Nils Dailey, N. Guilford; Kenneth Southall, Wethersfield; Timothy Webster, Norfolk; Gordon Leeke, Glastonbury; Chaokang Chu, West Hartford, all of Conn.

[73] Assignee: Cuno Incorporated, Meriden, Conn.

[*] Notice: The portion of the term of this patent subsequent to Jan. 29, 2002 has been disclaimed.

[21] Appl. No.: 384,846

[22] Filed: Jul. 21, 1989

Related U.S. Application Data

[63] Continuation of Ser. No. 190,556, Apr. 5, 1988, abandoned, which is a continuation of Ser. No. 903,914, Sep. 4, 1986, Pat. No. 4,743,373, which is a continuation of Ser. No. 723,691, Apr. 16, 1985, Pat. No. 4,675,104, which is a continuation-in-part of Ser. No. 693,904, Jan. 23, 1985, abandoned, which is a continuation of Ser. No. 505,532, Jun. 17, 1983, Pat. No. 4,496,461.

[51] Int. Cl.⁵ .............................. B01D 15/08
[52] U.S. Cl. .................. 210/198.3; 210/198.2; 210/502.1
[58] Field of Search ............ 210/635, 656, 657, 198.2, 210/502.1, 497.1, 494.3; 55/67, 197, 386; 162/181.6; 436/161, 162; 422/70

[56] References Cited

U.S. PATENT DOCUMENTS

| | | | |
|---|---|---|---|
| 2,564,637 | 8/1951 | Chase | 210/494.3 |
| 2,708,519 | 5/1955 | Novak | 210/198.2 |
| 2,835,393 | 5/1958 | Buckman | 210/494.3 |
| 3,415,384 | 12/1968 | Kasten | 210/494.3 |
| 3,483,986 | 12/1969 | Wright | 210/198.2 |
| 3,856,681 | 12/1974 | Huber | 210/198.2 |
| 3,966,609 | 6/1976 | Godbille | 210/198.2 |
| 4,113,627 | 9/1978 | Leason | 210/446 |
| 4,305,782 | 12/1981 | Ostreicher | 162/181.6 |
| 4,309,247 | 1/1982 | Hou | 162/181.6 |
| 4,354,932 | 10/1982 | McNeil | 210/198.2 |
| 4,384,957 | 5/1983 | Crowder | 210/656 |
| 4,496,461 | 1/1985 | Leeke | 210/198.2 |
| 4,675,104 | 6/1987 | Rai | 210/502.1 |
| 4,743,373 | 5/1988 | Rai | 210/502.1 |

Primary Examiner—Ernest G. Therkorn
Attorney, Agent, or Firm—Weingram & Zall

[57] ABSTRACT

A chromatography column for effecting chromatographic separation of at least two components of a sample flowing through the column. The column comprises a housing and at least one solid stationary phase within the housing. The stationary phase has chromatographic functionality and is effective for chromatographic separation. Means are provided for distributing the sample through the stationary phase and for collecting the sample after the sample has flowed through the stationary phase. The stationary phase comprises:

(a) a plurality of layers of swellable fibrous matrix in sheet form having chromatographic functionality and being effective for chromatographic separation; and (b) a spacer means between each layer for permitting controlled swelling thereof and enhancing the distribution of sample flowing through the stationary phase.

15 Claims, 5 Drawing Sheets

CHROMATOGRAPHY COLUMN

This application is a continuation of 07/190,556 filed Apr. 5, 1988, now abandoned, which is a continuation of 06/903,914 filed Sep. 4, 1986, now U.S. Pat. No. 4,743,373, which is a continuation of 06/723,691 filed Apr. 16, 1985,n ow U.S. Pat. No. 4,675,104, which is a continuation-in-part of 06/693,904 filed Jan. 23, 1985, now abandoned which is a continuation of 06/505,532 filed June 17, 1983, now U.S. Pat. No. 4,496,461.

BACKGROUND OF THE INVENTION

1. Field of the Invention

This invention relates to a novel molecular separation column, e.g. chromatography column, and more particularly to a novel column using a solid stationary phase.

2. Description of the Background Art

Chromatography is a general term applied to a wide variety of separation techniques based upon the sample interchange between a moving phase, which can be a gas or liquid, and a solid stationary phase. When gas is the moving phase (or "mobile phase" as referred to in chromatographic terminology), the technique is termed gas chromatography and when liquid is the mobile phase, the technique is termed liquid chromatography.

Separations can be classified into either analytical or preparative depending on the objective. In analytical separations, the objective is high resolution separation, identification and quantification of the various components of a sample mixture. In preparative chromatography, on the other hand, the objective is the isolation of large pure quantities of the desired constituents in the sample.

The collection of liquid chromatographic column techniques can be classified in several ways. The most fundamental is based on naming the types of phases used. Liquid absorption chromatography is used extensively for organic and biochemical analysis. Ion exchange chromatography is a special field of liquid-solid chromatography and is specifically applicable to ionic species. Affinity chromatography is based on the attraction (affinity) of a ligand bonded to the solid stationary phase for a given component of the sample. Liquid-liquid or partition chromatography involves the use of a thin layer of liquid held in place on the surface of a porous inert solid as the stationary phase.

In the chromatographic process, it is customary to pass a mixture of the components to be resolved in a carrier fluid through a chromatographic apparatus or a separative zone. The separative or resolving zone, i.e. the stationary phase, generally consists of a material referred to as a chromatographic media, which has an active chromatographic sorptive function for separating or isolating the components in the carrier fluid. The separative zone usually takes the form of a column through which the carrier fluid passes.

A major problem in the art of column chromatography is to obtain uniform fluid flow across the column. It has been recognized that the solution to this problem resides in an ability to obtain uniform packing, distribution and density of the chromatographic media within a column. To a large degree, the packing problem is surmounted in the laboratory chromatography columns by using columns having a small internal diameter, generally on the order of ⅛ inch to 1½ inches. In such columns, an uneven chromatographic fluid flow resulting from nonuniform packing of the chromatographic media is quickly relaxed across the column diameter and does not significantly affect analytical results.

To provide an economically feasible preparative chromatography column, the column diameter must be larger than one inch and preferably on the order of one foot or more. Attempts to scale analytical chromatography columns to a size feasible for preparative and/or production chromatography have met with substantial losses in column efficiency. It has been found that as the column diameter or cross-sectional area is increased, the separation or resolving power of the chromatography column decreases. The resolution losses can be attributed primarily to a lack of effective fluid flow distribution in the column.

Various internal column devices have been proposed to overcome the difficulties of producing large diameter preparative and production chromatography columns. Other approaches have been to provide homogeneous distribution of chromatographic media and maintenance of uniform media density across the column or to develop novel type media and/or packing.

Of recent date, the assignee herein has developed unique chromatographic media, comprising in its physical form a homogeneous fibrous matrix, preferably in sheet form. Such chromatographic media are described in the following U.S. patents and patent applications:

U.S. Pat. No. 4,384,957 to Crowder, III, et al.;

U.S. Pat. No. 4,512,897 to Crowder, III, et al.;

U.S. Pat. No. 4,404,285, entitled "Process For Preparing Zero Standard Serum" to Hou;

U.S. Pat. No. 4,488,969, entitled "Fibrous Media Containing Millimicron Sized Particles" to Hou;

U.S. Ser. No. 388,989, filed June 16, 1982, now U.S. Pat. No. 4,559,145, entitled "Process for Preparing a Zero Standard Serum" to Hou et al.;

U.S. Ser. No. 401,361, filed July 23, 1982, now U.S. Pat. No. 4,578,150, entitled "Fibrous Media Containing Millimicron Sized Particles" to Hou;

U.S. Ser. No. 576,448, filed Feb. 2, 1984, now U.S. Pat. No. 4,663,163, entitled "Modified Polysaccharide Supports" to Hou et al.;

U.S. Ser. No. 643,212, filed Aug. 22, 1984, now U.S. Pat. No. 4,687,820, entitled "Modified Polypeptide Supports" to Hou et al.;

U.S. Ser. No. 643,613, filed Aug. 22, 1984 entitled "Modified Siliceous Supports" to Hou et al.;

U.S. Ser. No. 656,922, filed Oct. 2, 1984, now U.S. Pat. No. 4,639,513, entitled "Intravenous Injectable Immunogloblin (IgG) and Method for Producing Same" to Hou et al.; and U.S. Ser. No. 665,402, filed Oct. 26, 1984, now U.S. Pat. No. 4,606,824, entitled "Modified Cellulose Separation Matrix" to Chu et al.

The entire disclosures of the foregoing commonly assigned patents and applications are incorporated herein by reference.

Crowder, III et al., in each patent, describes a chromatography column having a substantially homogeneous stationary phase which comprises a porous matrix of fiber having particulate immobilized therein. At least one of the fiber or particulate is effective for chromatographic separations. Preferably, the stationary phase comprises a plurality of sheets in disc form stacked inside a column. The edges of the discs cooperate with the interior wall of the column to form a substantially fluid tight seal therewith, thus preventing any appreciable skewing or by-pass of fluid around the edges of the elements. In its preferred form, the fluid tight seal is produced by the hydrophilic swelling of the stationary phase.

Hou (U.S. Pat. No. 4,404,285 and U.S. Ser. No. 388,989) describes a method for removing thyroid or steroid hormones from a serum by using a composite sheet, comprising a matrix of self-bonding fibers having dispersed therein carbon particles. The sheets are used preferably in the chromatographic column described in Crowder, III et al. and are also hydrophilic swellable discs or pads.

Hou (U.S. Pat. No. 4,488,969 and U.S. Ser. No. 401,361) describes a self-supporting fibrous matrix having immobilized therein at least about 5% by weight of micro particulate (average diameter less than 1 micron), preferably fumed silica or alumina. The media is also preferably used in the chromatographic columns disclosed in Crowder, III et al. and the solid stationary phase is also hydrophilic swellable.

Hou et al. (576,448) describe a polysaccharide material which comprises a polysaccharide covalently bonded to a synthetic polymer. The synthetic polymer is made from a polymerizable compound which is capable of being covalently coupled directly or indirectly to the polysaccharide and one or more polymerizable compounds. The polymerizable compound contains an ionizable chemical group, a chemical group capable of transformation to an ionizable chemical group or a chemical group capable of causing the covalent coupling of the compound to an affinity ligand or biologically active molecule. The media is capable of acting as a chromatographic support for ion exchange chromatography, for affinity chromatography or as reagents for biochemical reactors. Preferably sheets of this material are loaded into an appropriately sized cylindrical column to form the desired stationary phase in a manner similar to Crowder, III et al. The preferred solid stationary phase is also hydrophilic swellable.

All of these media in their preferred embodiment are fibrous matrices which are hydrophilic swellable, i.e. they tend to swell upon contact with aqueous systems. In a stacked disc type chromatographic column such swelling is useful in assisting producing a fluid tight seal with the interior wall of the column to form a water swellable fit therewith. Such a seal prevents skewing or bypass of the fluid around the edges of the elements.

In Hou et al. (576,448), it is indicated that the media could be used in a "jelly roll" type column, i.e. a sheet of media spirally wound around a foraminous core to form a cylinder having a plurality of layers around the axis thereof. It was subsequently found that the radial flow of a sample through such a "jelly roll" type solid phase was not evenly distributed, and there was substantial bypass of the fluid around certain areas of the media. It is believed that this is due to the swelling and resulting compression of the chromatographic media upon contact with the fluid flowing therethrough thus producing an irregular homogeneity in the solid stationary phase leading to an irregular hydrodynamic profile through the column and consequently to the establishment of preferential hydrodynamic routes which rapidly diminish the efficacy and selectivity of the chromatographic column.

Hou et al. (643,212) describes a modified polypeptide material which comprises a polypeptide covalently bounded to a synthetic polymer, which synthetic polymer is made from a polymerizable compound as described in Hou et al. (576,448). The material is capable of acting as chromatographic support for ion exchange chromatography, affinity chromatography and reverse phase chromatography or as reagents for biochemical reactors. The materials are disclosed as suitable, in sheet form, as the stationary phase for loading into chromatographic columns.

Hou et al. (643,613) describes a modified siliceous material which comprises a siliceous material covalently bound to a synthetic polymer, the synthetic polymer similar to that described in Hou et al. (576,448) and Hou et al. (643,212). The material is described as suitable for chromatographic separation media, the separation media comprising the stationary phase for chromatographic columns.

Hou et al. (656,922) describes a host of additional chromatographic media, many of which include the media disclosed in Hou et al. (576,448; 643,212; and 643,613). Additionally, this application describes further embodiments directed to specific affinity media, ion exchange media, and reverse phase media, all suitable for use in chromatographic separations in general and in the preparation of intravenous injectable IgG specifically.

Chu et al. (665,402) describes modified cellulosic materials which are essentially free of LAL reactive extractables.

Of additional relevance to this invention are the following references:

Wang et al., Biotechnology and Bioengineering XV, page 93 (1973), describes the preparatron of a "Bio-Catalytic Module" wherein collagen-enzyme membranes are layered on a supporting material, such as cellulose acetate membrane, and coiled around a central rod. Glass rods are used as spacers, which are so arranged that the distance between them is small enough to prevent the adjacent layers from contacting each other. After coiling the complex membrane upon the spacers, the cartridge is then fitted into a plastic shell to form a flow-through reactor configuration. The flow through the column is axial, i.e. the sample flowing through the column contacts the membrane in a cross-flow manner.

Wang et al. (page 583) also recognizes that the flow of sample through such a device is mainly parallel to the membrane surface and that some of the enzyme molecules located within the matrix may not be readily accessible. In order to improve the contact efficiency, Wang et al. suggests that the sample flow through the permeable membrane under hydraulic pressure. In this configuration of the reactor, a filter fabric serves as a backing material which separates successive layers of invertase-collagen membrane, thus preventing overlapping of the membrane layers. A perforated stainless steel tube is used as a central core element which is also used for feeding the sample. A uniform radial distribution of the substrate is achieved by metering flow through a number of holes drilled ninety degrees (90°) apart radially along the stainless tube. A spiral reactor configuration is formed by coiling alternate layers of the membrane and backing around the steel tube. The spiral cartridge is fitted into a plexiglass outer shell. The plastic housing is affixed to two threaded aluminum end plates. The sample is fed from the central tube while the reaction product is collected through a central port located on the periphery of the reactor shell.

U.S. Pat. No. 3,664,095 to Asker describes a packing material which may be spirally wound around a central axis for fluid treatment such as drying, heat exchange, ion exchange, molecular sieve separations and the like.

Flow is axial through the apparatus, i.e. parallel to the surface of the packing material.

U.S. Pat. No. 3,855,681 to Huber describes a preparative and production chromatography column which includes a relatively inert inner core onto which is wound in a spiral pattern a relatively inert sheet of material, such as synthetic polymeric film. Prior to winding, the film is coated with a chromatographic media. A thickness dimension of the chromatographic media is arranged substantially perpendicular to the primary direction of fluid flow through the column, i.e. flow is axial thereof and thus parallel to the surfaces of the chromatographic media.

U.S. Pat. No. 4,242,461 to Bartoli et al. describes a reactor for effecting enzymic reactions in which the flow of the solution to be treated through the catalytic bed takes place radially. It is preferred to have the catalytic bed in the form of coils of enzyme-occluding fibers. The catalytic bed is formed by winding fibers on which the enzymes are supported, so as to form coils with filaments or groups of filaments arranged helically. The fibers inserted in the reactor can also support, instead of enzymes, chelation agents, antibodies, or similar products which are immobilized, like the enzymes, by physical bonds, ion exchange, absorption or occlusion in the filamentary polymeric structures.

U.S. Pat. No. 4,259,186 to Boeing et al. (1981) describes an elongated gel filtration column having an outer wall and at least one gel chamber defined therein and adapted to be filled with a filter gel. The gel chamber is sub-divided by a plurality of interior partition walls arranged in parallel to the column wall. The partition walls are of a length shorter than the length of the gel chamber.

U.S. Pat. No. 4,299,702 to Bairingi et al. (1981) describes a liquid separation apparatus of the spiral type employing semi-permeable membrane sheets, between which a spacing layer is located, and utilizing the principal of reverse osmosis or ultrafiltering for separating a desired liquid component, i.e. a solvent or a solute, from a pressurized feed solution. In this type of apparatus, the feed flows substantially spirally through the apparatus, i.e. parallel to the membrane. See also U.S. Pat. No. 4,301,013 to Setti et al. (1981).

None of these references describe the problems associated with the use of a swellable fibrous matrix chromatographic media in sheet form, particularly utilized in a "jelly roll" type column nor the solution to such problems. Further, none of the references address the problems of multiple layers of swellable chromatographic media.

OBJECTS AND SUMMARY OF THE INVENTION

It is an object of the invention to provide an efficient preparative or production chromatography column using a solid stationary phase which is in cartridge form, which may be disposable.

Another object of this invention is to provide a solid stationary phase of a chromatography column which can be made in cartridge form, which may be disposable.

A further object of this invention is to provide a chromatography column which has a solid stationary phase which provides even distribution of a sample flowing through the stationary phase.

Still a further object of this invention is to provide a chromatographic column which accommodates a swellable fibrous matrix in sheet form as the solid stationary phase.

Another object of this invention is to provide a chromatography column which has a reduced pressure drop, enhanced flow and enhanced capacity.

A further object of this invention is to provide a chromatography column having essentially no determined diametric size limitation, which can be quickly and relatively inexpensively manufactured.

A still further object of this invention is to provide a chromatography column which resolves the uneven fluid flow problems encountered when attempting to scale up analytical columns to preparative and production columns.

Yet another object of the present invention is to provide a solid stationary phase for liquid chromatography which ensures that substantially all of the chromatographic media is utilized.

A further object of the invention is to provide an inexpensive, high quality chromatographic column which can be a disposable item in many, perhaps most, processing situations The foregoing objects of this invention are accomplished by a chromatography column for effecting chromatographic separation of at least two components of a sample flowing through the column. The column comprises a housing and at least one solid stationary phase within the housing. The stationary phase has chromatographic functionality and is effective for chromatographic separation. Means are provided for distributing the sample through the stationary phase and for collecting the sample after the sample has flowed through the stationary phase. The stationary phase comprises:

(a) a plurality of layers of a swellable matrix in sheet form having chromatographic functionality and being effective for chromatographic separation; and (b) a spacer means between each layer for permitting controlled swelling thereof and enhancing the distribution of sample flowing through the stationary phase.

The solid stationary phase may be fabricated into a cartridge form for replacement in the housing. A plurality of cartridges may be used either in series or parallel flow configuration in a single housing.

In one embodiment, the chromatography column for effecting chromatographic separation of at least two components of a sample flowing therethrough comprises a housing and at least one solid stationary phase having chromatographic functionality and effective for chromatographic separation within said housing. The housing comprises an inlet member having a sample inlet and a distribution means in communication with said sample inlet means, said distribution means substantially uniformly distributing said sample therethrough, and an outlet housing member having a sample outlet means and a sample collection means in communication with said sample outlet means. In one preferred embodiment, the sample inlet means and sample outlet means form a radially outwardly expanding stationary phase chamber.

The stationary phase comprises one or more layers of a swellable fibrous matrix in sheet form, each layer having chromatographic functionality and being effective for chromatographic separation. Where the stationary phase comprises a plurality of layers, said layers may be separated from each other by a spacer means, said spacer means permitting controlled swelling of said layers of swellable fibrous matrix in sheet form. However, the stationary phase and housing coact to provide substantially uniform radial distribution of the sample.

BRIEF DESCRIPTION OF THE DRAWINGS

Further characteristics, features and advantages of the invention, as well as other objects and utilities, will become readily apparent to those skilled in the art from consideration of the invention as described herein and illustrated by the following drawings.

DETAILED DESCRIPTION OF THE INVENTION

The solid stationary phase in this invention comprises a swellable fibrous matrix in sheet form. Preferably, this sheet is homogeneous or substantially homogeneous, which in effect means that the stationary phase is of a uniform or substantially uniform structure and/or composition.

Figure 1:
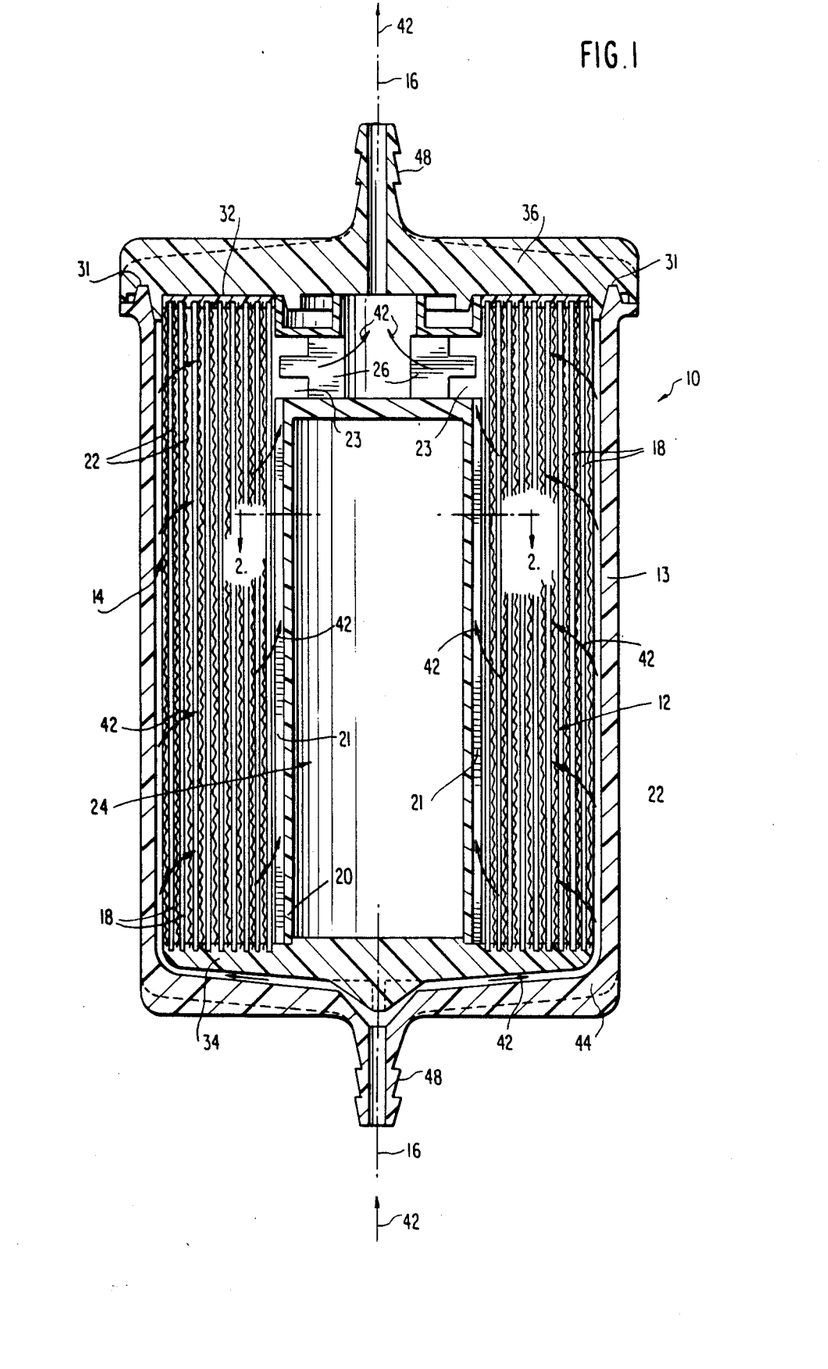
FIG. 1 is a partial sectional view of a side elevation of one embodiment of the chromatography column of this invention.
Figure 2:
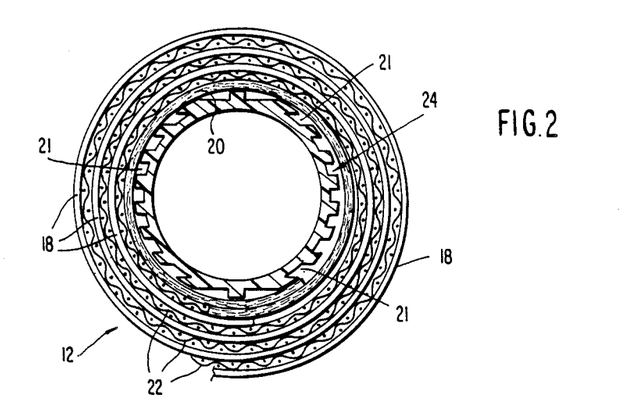
FIG. 2 is an enlarged cross-sectional view taken along line 2—2 of FIG. 1.
Figure 3:
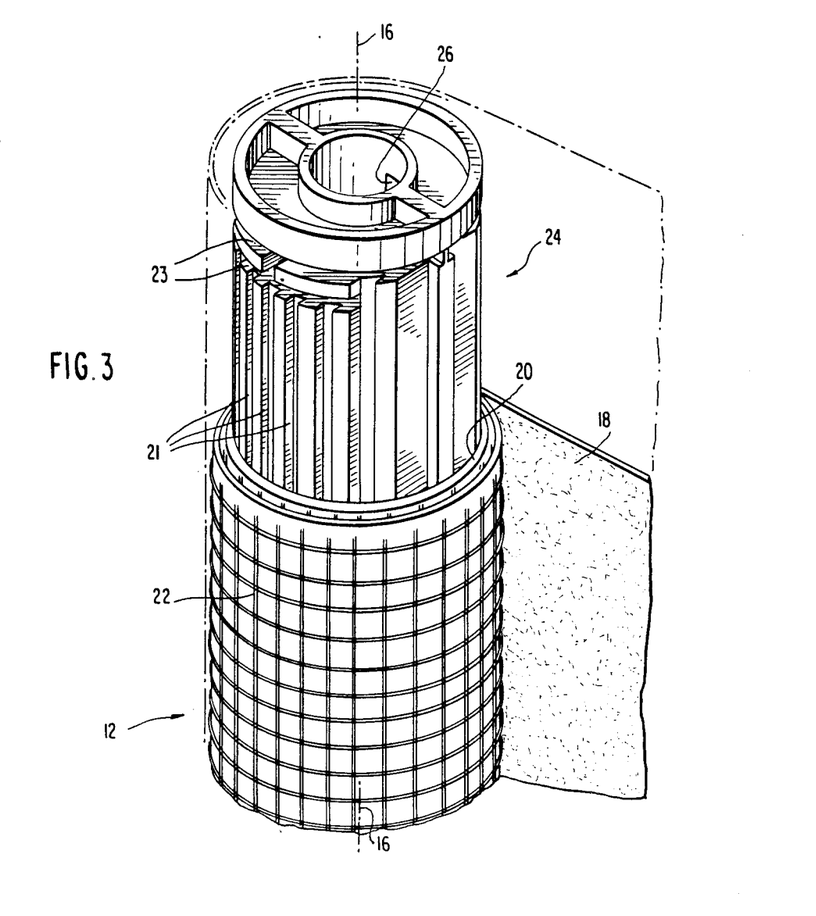
FIG. 3 is a perspective view of the core with a portion of the solid stationary phase broken away therefrom showing the spirally wound chromatographic media and spacer means therebetween.

Referring to the drawings, wherein like character references indicate like parts, FIGS. 1 through 3 depict one embodiment of the chromatography column of this invention. Referring to FIG. 1, the column, which may be in cartridge form, generally designated 10, is comprised of a cylindrical stationary phase 12, and cylindrical tube 13, which form a cylindrical chamber 14 which acts as a housing for the stationary phase 12. The solid stationary phase 12 can be inserted into chamber 14 formed by a glass, metal or polymeric tube or cylinder 13 having a diameter somewhat larger than the external diameter of the stationary phase 12. Suitable fluid admission, collection and monitoring systems can also be employed with the column as in conventional analytical and preparative columns. The stationary phase 12 is positioned within the chamber 14 and preferably has a longitudinal axis 16 coaxial with the axis of the cylindrical chamber 14. Optionally, a plurality of cartridges may be placed in a single housing in various configurations to effect parallel and/or series flow between the cartridges (not shown). The solid stationary phase has chromatographic functionality and is effective for chromatographic separation.

Referring to FIGS. 2 and 3, the stationary phase 12 is constructed of a swellable fibrous matrix 18, usually hydrophilic swellable, in sheet form which is the active media for chromatographic separation. The chromatographic media in sheet form 18 is sandwiched between a single non-woven mesh 22 or plurality of mesh. The composite sheet of chromatography media 18 and mesh 22, preferably non-woven, is spirally wound around a cylindrical core 24 having a longitudinal axis 16 to form a plurality of layers around the axis 16. The core 24 is provided with a plurality of longitudinal and axially oriented channels 21 for directing the liquid into circumferential channels 23 which are in fluid communication with core 24. The mesh 22, due to the open areas and thickness thereof, acts as a spacer means between each layer of media 18 which permits the controlled swelling of the media and enhances the distribution of the sample flowing through the stationary phase 12. The cylindrical core 24 is provided with apertures 26 near the top thereof for the flow of sample from the circumferential channels 23 into the open interior of the core.

Referring to FIG. 1, the wound composite sheet 18 and 22 and core 24 are then capped by stationary phase end caps 32 and 34. The stationary phase end caps 32 and 34 of this subassembly are sealed by thermoplastic fusion to the core 24 and also to the ends of the composites 18 and 22. The subassembly, comprising 18, 22, 24, 32 and 34 is then slipped into chamber 14. The cylinder end cap 36 is then thermoplastically fused to the top edge 31 of cylinder 13. The fluid or sample 42 can thus flow radially from the outside through the solid stationary phase to the open channel 21 of core 24, since the interior and exterior are completely separated by the solid stationary phase and sealed off by stationary phase end caps 32 and 34.

The preformed stationary phase end caps 32 and 34 are preferably applied to the cylindrical solid stationary phase 12 by heating an inside face of the thermoplastic stationary phase end cap to a temperature sufficient to soften a sufficient amount of the stationary phase end cap to form a thermoplastic seal with the ends of the core 24 and composite sheet 18 and 22. All of the edges are then embedded into the softened material. The softened material is then hardened, typically by ambient conditions, to form a thermoplastic sealing relationship between the sealing surface of the stationary phase end caps 32 and 34, the core 24 and the ends of the solid stationary phase 12 to form a leak-proof seal. Such methods of applying stationary phase end caps are well known in the filtration art. See, for example, U.S. Ser. No. 383,383 and U.S. Ser. No. 383,377, filed on May 28, 1982, to Meyering et al. and Miller, respectively. Optionally, the stationary phase end caps can be molded integrally in situ onto the solid stationary phase.

Stationary phase end caps of thermoplastic materials are preferred because of the ease of bonding, but it is also possible to use thermo-setting resins in a thermoplastic, fusible or heat-softenable stage of polymerization, until the bondings have been effected, after which the curing of the resin can be completed to produce a structure which can no longer be separated. Such a structure is autoclavable without danger of destroying the fluid tight seal, the solid stationary phase 12, and the stationary phase end caps 32 and 34. Thermoplastic resins whose softening point is sufficiently high so that they are not softened under sterilizing autoclaving conditions are preferred for biomedical use. Exemplary of the plastic materials which can be used are polyolefins.

Referring to FIG. 1, the preferred column 10 has a stationary phase end cap 34 on one end which does not open to the exterior of the subassembly 18, 22, 24, 32, and 34 but is closed off. This stationary phase end cap 34 can nest on the bottom end wall 44 of cylinder 13 while still permitting the flow of sample 42 into chamber 14 around the outside of stationary phase 12, or this lower stationary phase end cap 34 of the subassembly 18, 22, 24, 32 and 34 is in spaced apart relationship from the bottom end wall 44 of cylinder 13, thus permitting the flow of sample 42 into the chamber 14.

The upper end of cartridge 40 has a cylinder end cap 36 which is in fluid communication with channels 21 of cylindrical core 24 thus permitting the flow of fluid from the outer periphery of cylindrical core 24 to the center of core 24 to the outside of cylinder end cap 36. The cylinder end cap 36 has molded thereon fitting 48 for fluid connection through a collection means (not shown).

Referring to FIG. 2, prior to winding the chromatography media 18 on the core 24, the exterior surface of core 24 may be completely wrapped with a scrim material 20. Additionally, after winding the chromatography media 18 on the core 24, the exterior surface thereof may be completely wrapped with mesh material 22.

FIGS. 4 through 10 depict another embodiment of the chromatography column of this invention, the embodiment wherein the column is in disc configuration, again wherein like character references indicate like parts.

Referring to FIGS. 4-10, the column in disc configuration, generally designated 110, comprises an inlet housing member 112, an outlet housing member 114, and a stationary phase 116.

Figure 4:
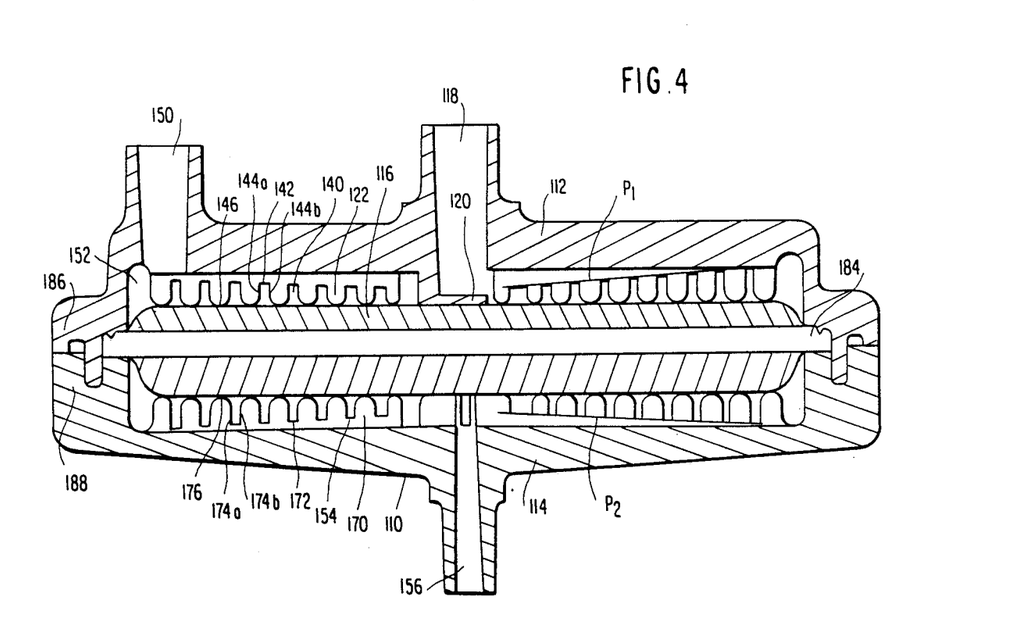
FIG. 4 is a cross-sectional view of another embodiment of the invention wherein the chromatography column is in disc configuration.
Figure 5:
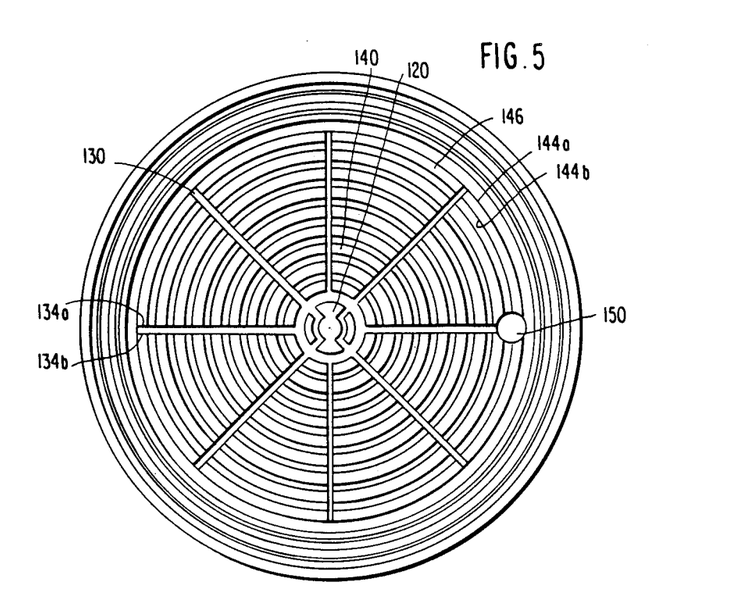
FIG. 5 is a top plan view of the inlet housing member of the invention embodiment in disc configuration.

The inlet housing member 112 comprises a sample inlet means 118, baffle means 120, and sample distribution means 122. The sample inlet means 118 is in communication with the sample distribution means 122.

The sample distribution means 122 comprises plural radial distribution channels or grooves 130 and plural concentric distribution channels 140, the radial distribution grooves 130 and concentric distribution channels 140 being in communication with each other and with inlet means 118. Radial distribution grooves 130 comprise distribution groove bottom portions lying a plane represented by line $P_1$ in FIG. 4 and $P_1$ in FIG. 10, and distribution groove wall portions 134a and 134b. Concentric distribution channels 140 comprise concentric distribution channel bottom portions 142, concentric distribution channel wall portions 144a and 144b, and concentric distribution channel apex portions 146.

Optionally, the inlet housing member 112 may contain a venting means 150, the function and operation of which will be defined below. The venting means is in communication with a chamber 152. Chamber 152 is formed by inlet housing member 112 and outlet housing member 114 (see FIGS. 4 and 10). Chamber 152 contains the stationary phase 116.

Figure 6:
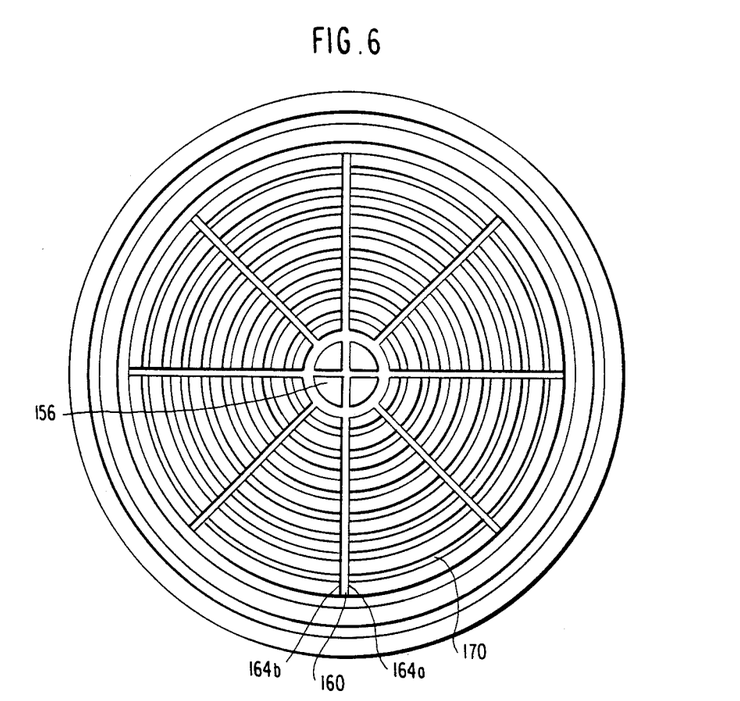
FIG. 6 is a top plan view of the outlet housing member of the invention embodiment in disc configuration.

The outlet housing member 114 comprises a sample collection means 154 and sample outlet means 156, sample collection means 154 being in communication with sample outlet means 156.

Sample collection means 154 comprises plural radial collection grooves 160 and plural concentric collection channels 170. Radial collection grooves 160 and concentric collection channels 170 are in communication with each other and with sample outlet means 156.

Figure 10:
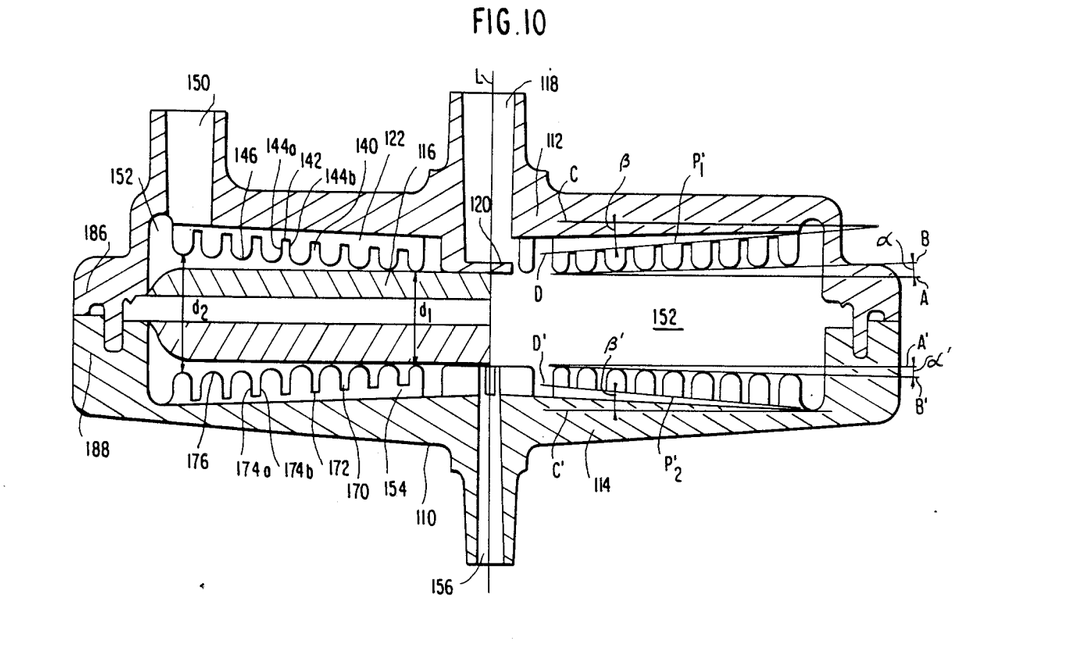
FIG. 10 is a cross-sectional view of a preferred configuration for the invention column in disc configuration. In this configuration, the housing in disc configuration forms a radially outwardly expanding chamber. A portion of the spacer means is removed for clarity.

Radial collection grooves 160 comprise radial collection groove bottom portions lying in a plane represented by line $P_2$ in FIG. 4 and $P_2$ in FIG. 10, and radial groove wall portions 164a and 164b. Concentric collection channels 170 comprise concentric collection channel bottom portions 172, concentric collection channel side wall portions 174a and 174b and concentric collection channel apex portions 176.

Figures 7, 8:
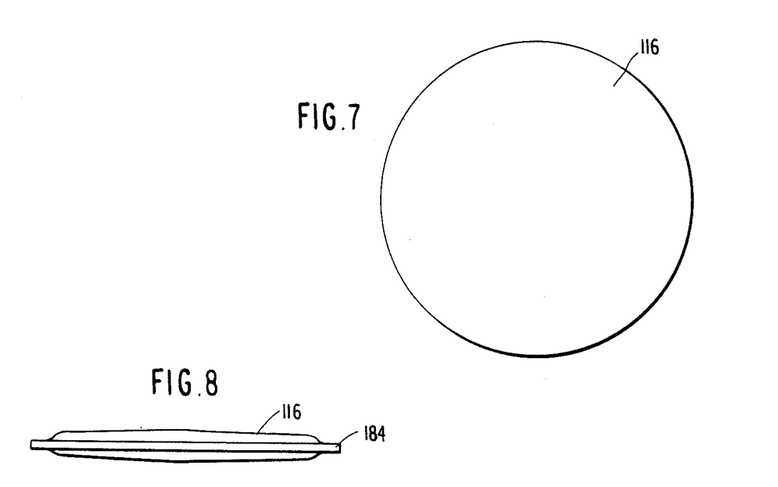
FIG. 7 is a top plan view of one embodiment of the stationary phase of the invention column in disc configuration.
FIG. 8 is a side elevation of one embodiment of the stationary phase of the invention column in disc configuration.
Figure 9:
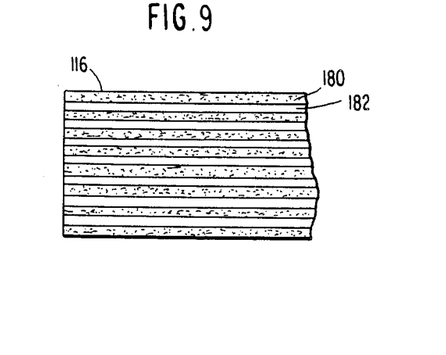
FIG. 9 is a cross-sectional view of one embodiment of the stationary phase of the invention column in disc configuration depicting a plurality of layers of separation media and spacer means interposed between adjacent layers of said separation media, prior to the sonic welding of the peripheral edges.

Stationary phase 116 has chromatographic functionality and is effective for chromatographic separation. Referring to FIGS. 7, 8 and 9 in particular, the stationary phase 116 may comprise a plurality of layers of a swellable fibrous matrix 180 in sheet form, having chromatographic functionality and being effective for chromatographic separation, and a spacer means 182 between each adjacent layer of swellable fibrous matrix 180. This configuration is best shown in FIG. 9, a cross-sectional view of one embodiment of the separation phase 16.

The swellable fibrous matrix 180 is preferably hydrophilic swellable and comprises the active media for chromatographic separation. The spacer means 182 may be typically a woven or non-woven mesh similar to mesh 22 of FIGS. 2 and 3 above and is further described below. The mesh, due to the openness and thickness thereof, acts as a spacer means between each layer of swellable fibrous matrix 180 and permits the controlled expansion thereof without closing off the porous structure of the media, thereby enhancing the distribution of the sample flowing through the stationary phase 116.

As may be seen from FIG. 8, a typical manner of conforming the stationary phase 116 is to produce a "sandwich" of alternating layers of swellable fibrous matrix in sheet form and layers of spacer means, with the periphery of the sandwich compressed into a fluid tight configuration 184. Typically, the peripheral edges of alternating discs of swellable fibrous matrix 180 and spacer means 182 are joined. Preferably, the fibrous matrix 180 contains or has bonded therein a thermoplastic polymeric material. Similarly, in a preferred embodiment, spacer means 182 also is made of or contains thermoplastic polymeric materials. In this configuration, the edges may be uniformly joined by appropriate heat treating, e.g. sonic welding. As may be seen from FIG. 4, in a preferred embodiment, the fluid tight peripheral configuration 184 is itself contained in a fluid tight, hermetic seal formed by the mating edges 186 and 188 of, respectively, the inlet housing member 112 and the outlet housing member 114. In this manner, sample entering through inlet means 118 must pass through stationary phase 116 prior to exiting through outlet means 156.

The disc configured chromatography column of FIGS. 4-9 is formed using conventional and well known fabrication techniques. Typically, the stationary phase 116, a preformed "sandwich" of alternating layers of swellable fibrous matrix and spacer means, with peripheral edges sonically welded and configured as in FIG. 8, is placed in inlet housing 112 and outlet housing member 114 is placed thereover. Subsequently, the mating edges 186 of the inlet housing member 188 and of the outlet housing member 190 are joined to form an airtight and fluid tight seal. In one embodiment, the edges are sealed by sonically welding same, the technique described in Branson Sonic Power Company, Danbury, CT, Information Sheet PW-3, 1971, incorporated by reference herein.

Vent means 150, as mentioned above, represents an optional configuration of the disc embodiment of the column. Its purpose is to allow air in the column to exit the column during use. Typically, vent means 150 is adapted to be sealed off when all air has been removed from the system. In an alternative embodiment, vent means 150 contains a hydrophobic media which will allow the passage of gases but not liquids, as disclosed in U.S. Pat. No. 4,113,627, incorporated herein by reference.

In a preferred embodiment, depicted by FIG. 10, chamber 152 is radially outwardly expanding. By the term "radially outwardly expanding" is meant that the volume at the interior chamber is less than the volume at the periphery of the chamber. In this configuration, referring to FIG. 10, the distance between distribution means 112 and collection means 114 at the interior, $d_1$, is less than the distance between distribution means 112 and collection means 114 at the periphery $d_2$.

Because the stationary phase 116 is hydrophilic swellable, sample solution on contact with separation phase 116 causes the separation phase to swell. As the separation phase swells, the pressure differential between the inlet and outlet sides of the separation media increases, thereby restricting sample flow-through. By designing a housing as described above, i.e. in radially outwardly expanding configuration, the pressure differential between the inlet and outlet sides of the stationary phase decreases towards the periphery, thereby maximizing utilization of the chromatographic separation function of the stationary phase and substantially increasing the adsorption capacity of a given unit.

In another preferred embodiment, also depicted in FIG. 10, the volume of each succeeding concentric distribution channel 140 and concentric collection channel 170 increases from the interior to the periphery of the chromatographic column. In this manner, clogging of the channels by the swelling of the hydrophilic swellable stationary phase is vitiated, thereby promoting uniform distribution of sample and maximum utilization of column capacity.

In the embodiment depicted in FIG. 10, lines A, A', C and C' are lines which represent cross-sectional view of parallel planes which are perpendicular to the longitudinal axis L of the chromatography column. Lines B and B', respectively, represent cross-sectional views of planes which are substantially tangent to the apices 146 and 176 of concentric distribution channels 140 and concentric collection channels 170. Planes B and B' form angles $\alpha$ and $\alpha'$ with planes A and A'. Thus, planes B and B', at angles $\alpha$ and $\alpha'$ to planes A and A', respectively, define a radially outwardly expanding chamber 152, which in turn defines the limits of expansion of stationary phase 116. As described above, the optimal configuration for the radially outwardly expanding embodiment is such that stationary phase 116, in maximally swelled status, is just touching the most peripheral apices 146 and 176. It is to be understood that angles $\alpha$ and $\alpha'$ may be the same or different and may vary with the number of layers of qwellable fibrous matrix and the particular matrix in use. Typically, $\alpha$ and $\alpha'$ are about 2½°.

Lines D and D', respectively, represent cross-sectional views of planes which contain concentric distribution channel bottom portions 142 and concentric collection channel bottom portions 172 and define angles $\beta$ and $\beta'$ with planes C and C'. Thus, planes D and D', at angles $\beta$ and $\beta'$ to planes C and C', respectively, define the slope of the increasing depth of channels 140 and 170. In the embodiment of FIG. 10, $\beta$ and $\beta'$ are typically each about 5°. However, these angles may be varied, both with respect to one another and absolutely.

In similar manner, it is within the scope of the present invention to configure a chromatographic column such that radial distribution grooves 130 and/or radial collection grooves 160 increase in volume from the interior to the periphery of the column. Such a configuration is disclosed in U.S. Pat. No. 3,361,261, incorporated by reference herein.

As is understood by those skilled in the art, it is desirable to minimize the hold-up volume of a chromatographic column. With this in mind, an optimal design for a radially outwardly expanding chamber is that where the distance $d_2$ is such as to allow the swellable stationary phase to swell to its maximum, but with no unused space left. In this manner, the pressure differential at the periphery is minimized, minimized, while at the same time reducing hold-up volume to its lower limit as well. This housing configuration permits as well the use of a single layer of fibrous matrix or a plurality of layers of fibrous matrix with no spacer means interposed between layers. The radially outwardly expanding chamber coacts with the thus configured stationary phase to uniformly distribute sample thereacross.

The present invention as conceived utilizes known media and known media preparation techniques, specifically those described in the aforementioned co-pending applications and patents. This preferred media is fibrous, in sheet form and generally has the characteristics that it is hydrophilic swellable. The preferred chromatographic media is that described in the aforementioned Crowder, III et al. patents and Hou and Hou et al. applications and patents. It should be realized, however, that this invention is applicable to any type of swellable media in sheet form, whether it is hydrophilic swellable or otherwise.

In order to provide a chromatographic media matrix which is coherent and handleable, it is desirable that at least one of the components which go into forming the porous matrix be a long, self-bonding structural fiber. Such fiber gives the stationary phase sufficient structural integrity in both the wet "as formed" condition and in the final dry condition. Such a structure permits handling of the phase, in particular a sheet, during processing and at the time of its intended use. Preferably, the sheets which form the chromatographic media are formed by vacuum felting an aqueous slurry of fibers. The sheets may also be pressure felted or felted from a non-aqueous slurry. The sheet shows a uniform high porosity, with excellent flow characteristics, and is substantially homogeneous. In general, the media can range in thicknesses from about 5 mils to about 150 mils (dry); however, thicker or even thinner media may be utilized provided the sheet can be spirally wound or layered to produce a column which can perform as described above. The media can swell to at least 25% this thickness, and generally greater, e.g. two to four times, this thickness.

It is important when constructing the chromatography column of this invention that the chromatographic media used in the column be of uniform thickness throughout its length and width and that the media have a substantially uniform density throughout. It is preferred that the layer of media be substantially homogeneous with respect to itself; however, for certain applications and material, it is understood that non-homogeneous construction may be employed.

Since the solid stationary phase is intended in use to effect separation by maintaining a substantial pressure differential across the solid stationary phase, it is essential that the solid stationary phase have a sufficient degree of compressive strength to withstand deformation under such loads as may be imposed upon it. Such compressive strength must not only exist in the media itself but in the spacer means and the internal core upon which the chromatography media, or solid stationary phase is compressed.

Due to the swellability of the media, a key element of this invention is the spacer means between each layer of the media and/or the coaction of the chamber wall and the fibrous matrix. The spacer means permits controlled expansion of the media and enhancement of the distribution of sample flowing through the stationary phase. The spacer means located between each layer of the swellable chromatographic media provides for the distribution movement of the sample as the sample passes through the solid stationary phase. The spacer means functions to uniformly control thickness and density of the chromatographic media during use. In addition, the spacer means can serve as a backing or support for the layer of chromatographic media. This latter aspect is particularly useful during the manufacturing phase.

It is preferred that the spacer means be composed of a material which is inert with respect to the chromatographic process. By inert, it is meant the material does not adversely affect the function of the solid stationary phase.

Referring to FIGS. 2 and 3, the spacer means comprises the mesh 22. Alternatively, where the column design is as depicted in FIGS. 4-10, the spacer means 182 may also comprise a mesh, or scrim and mesh. A scrim material can function to channel, to a certain extent, the sample flowing through the media and substantially evenly disperse the sample axially and circumferentially across the media. The mesh material provides spacing between the media to permit controlled expansion thereof to prevent the "cut-off" to flow therethrough by compression of the permeable media and also assists in distributing or channeling the sample flowing through the media.

The mesh material is an open type of material having openings ranging, for general guidance, from 1/16 inch to ¼ inch.

It should be noted that the thickness of the spacer means, i.e. the scrim and particularly the mesh material, and the pore size of each to be used may be readily determined by one skilled in the art by performing tests which vary these factors. Such factors as the openness and thickness of these spacer means are highly dependent on the type of media utilized, e.g. swellability, wettability, thickness, chemical composition, etc., the flow rate of the sample through the stationary phase, the surface area of the stationary phase, e.g. number of windings, thickness of media, diameter of stationary phase, etc. It is thus very difficult to clearly specify these variables, other than to say that these may be determined by either trial and error or more elaborate testing procedures to determine the optimum parameters.

The preferred mesh material, at this time, is polypropylene CONWED (Grade TD-620).

The overall width of the stationary phase in accordance with the present invention can be infinite, the actual diameter being limited only by practical considerations such as space requirements. Since the diameter or width of the overall column can be increased without theoretical limitation, the sample size or amount of substance to be separated in the bed is not limited. Thus, the diameter can be increased to separate the desired amount of sample substance to be produced.

In operation, the sample is driven through the stationary phase and separated into distinct chromatographic fractions by the chromatographic media. The spacer means induces and permits flow of this stream as it moves through the column and therefore provides for improved resolution and utilization of the media's potential capacity.

Referring to FIG. 1, the sample is preferably introduced at the bottom of the column flowing to the outer surface of the solid stationary phase and then flowing radially inward through the layers of chromatographic media and spacer means into the channels 21 of core tube 24 and is withdrawn centrally. It is apparent, from what has been set forth above, that the radial flow can also be caused to circulate in the opposite direction.

Referring to FIG. 4, sample is preferably introduced at the inlet 118, passes to distribution means 122, is substantially uniformly distributed over the surface of the stationary phase 116 by radial distribution grooves 132 and concentric distribution channels 130, and passes through radial collection grooves 140 and concentric collection channels 170 and exits through outlet 156.

The chromatographic columns of this invention may be used for any of the well-known chromatographic separations usually performed with conventional columns. Additionally, the columns of the present invention may be found useful in the areas where conventional columns are impractical.

The novel columns of this invention can be used for separations in the analytical and preparative fields. The columns can be connected to all common types of chromatographic equipment. Several columns or cartridges of solid stationary phase can be connected in series or parallel. In large units, the columns can contain identical or different chromatographic media and can be of identical or different length and/or diameter.

It has been found that the aforedescribed stationary phase produces unexpected results in that the flow of sample through the column is enhanced without destroying the adsorptive capacity of the media. Additionally, when protein and dye staining tests were performed it was found that the stationary phase of this invention provided even distribution of sample flow therethrough without an increase in pressure drop when compared to a stationary phase not utilizing the spacer means described herein.

From the foregoing, it can be seen that a convenient stationary phase configuration has been invented which is easy to install, operate, and disassemble and is easily adaptable to any batch size or continuous type operation by the use of multiple configurations. Additionally, the chromatography column has excellent structural integrity.

The stationary phases decrease total processing time and when used with the proper chromatographic media has excellent binding capacity. The stationary phases may be used with standard type pumps, gravity feed, or syringes, utilized, in their preferred mode, at from 1 to 50 PSI, and even under vacuum. The stationary phases of chromatographic media are totally enclosed and completely self-contained to ensure sterile conditions. Due to the fact that the solid stationary phase is manufactured in a factory and assembled therein, each is virtually identical to the other, does not vary as in previously known columns and eliminates the dependence upon packing expertise. Additionally, there is no premeasuring of chromatographic media, no media loss due to handling, no packing problems, no fines generation and removal within the column and other problems associated with packing chromatographic columns. The column is simple to operate, does not produce any channeling by passing or shifts in bed volume. The chromatographic stationary phase allows scale up from milligram laboratory quantities to megagram production quantities. The stationary phase provides rigidity and strength and is particularly useful as a high flow, medium pressure matrix and is highly suitable for large scale protein or non-protein purifications.

It has surprisingly been found that when a column configured as in FIG. 10 is employed, the actual capacity is substantially increased over that of the column of FIG. 4. In this way, the actual capacity more closely approximates the theoretical capacity of the column. By configuring the column to maximize sample distribution, minimize hold-up volume, and maximize stationary phase utilization by creating a differential pressure gradient which decreases from the interior to the periphery, the useful and effective life of the column is substantially improved.

The present invention has been described in relation to several embodiments. Upon reading the specification, one of ordinary skill in the art would be able to effect various alterations, or changes in, or substitutions of equivalents to the present invention as disclosed. It is intended that the invention as conceived be limited only by the definition of the invention contained in the appended claims.

What is claimed is:

1. A chromatography column for chromatographic separation of at least two components of a sample flowing therethrough comprising:
   (1) a housing, the housing comprising:
      (a) an inlet housing member having an outer periphery;
      (b) an outlet housing member having an outer periphery;
      (c) the inlet housing member and the outlet housing member overlying each other to define a stationary phase chamber;
      (d) means for distributing the sample through the stationary phase chamber; and
      (e) means for collecting the sample after the sample has flowed through the stationary phase chamber;
   (2) a stationary phase within the chamber and having an outer periphery, the stationary phase comprising at least one layer of a swellable fibrous matrix in sheet form having chromatographic functionality and being effective for chromatographic separation and containing at the outer periphery thereof a thermoplastic polymeric material;
   wherein the stationary phase outer periphery is between the outer peripheries of the inlet and outlet housing members and forms a fluid tight mermetic thermoplastic seal between the outer peripheries of the inlet and outlet housing members formed by heating the outer periphery of the stationary phase.

2. The column of claim 1, wherein the stationary phase comprises:
   (a) a plurality of layers of swellable fibrous matrix; and
   (b) a spacer means having an outer periphery between each layer of swellable fibrous matrix for permitting controlled swelling thereof and enhancing the distribution of sample flowing through the stationary phase, and
   the spacer means comprising a thermoplastic polymeric material in the outer periphery thereof.

3. The column of claim 1 wherein the swellable fibrous matrix comprises a polysaccharide covalently bonded to a synthetic polymer having the chromatographic functionality, the synthetic polymer being the thermoplastic polymeric material contained in the fibrous matrix.

4. A chromatography column for effecting chromatographic separation of at least two components of the sample flowing therethrough comprising:
   (1) a housing, the housing comprising:
      (a) an inlet housing member having an outer periphery; and
      (b) an outlet housing member having an outer periphery;
      (c) the inlet housing member and the outlet housing member overlying each other to define a stationary phase chamber;
   (2) a stationary phase within the chamber comprising at least one layer of a swellable fibrous matrix in sheet form having an outer periphery and having chromatographic functionality and being effective for chromatographic separation;
   the inlet housing member comprising overlying the matrix, a means for distributing the sample through the stationary phase matrix, the means comprising radial distribution grooves and concentric distribution channels, the grooves and channels being in communication with each other; and
   the outlet housing member comprising underlying the matrix, a means for collecting the sample after the sample has flowed through the stationary phase, the means comprising radial collection grooves and concentric collection channels, the radial collection grooves and concentric collection channels in communication with each other;
   wherein the distance between the concentric distribution channels and the concentric collection channels increases from the interior of the stationary phase chamber to the outer periphery of the chamber to provide a radially outwardly expanding chamber which coacts with the stationary phase to provide substantially uniform radial distribution of the sample across the stationary phase.

5. The column of claim 4 wherein the stationary phase comprises:
   (a) a plurality of layers of a swellable fibrous matrix; and
   (b) spacer means between each layer of swellable fibrous matrix for permitting controlled swelling thereof, and enhancing the distribution of sample flowing through the stationary phase.

6. The column of claim 5 wherein the spacer means comprises:
   (a) a scrim layer for channeling the sample flow through the matrix and to substantially evenly disperse the sample; or
   (b) a mesh layer to provide a spacing between the layers to permit controlled expansion thereof and assist in distributing the sample; or
   (c) (a) in combination with (b).

7. The column of claim 5 wherein the spacer means comprises a mesh layer to provide spacing between the layers to permit controlled expansion thereof and assist in distribution of the sample.

8. The column of claim 4 wherein the inlet housing member further comprises a venting means.

9. The column of claim 4 wherein the swellable fibrous matrix is hydrophilic swellable.

10. The column of claim 9 wherein the swellable fibrous matrix swells to at least about 25% of its thickness.

11. The column of claim 4 wherein the stationary phase is an ion exchange stationary phase.

12. The column of claim 4 wherein the stationary phase is an affinity stationary phase.

13. The column of claim 4, wherein the outer periphery of the stationary phase contains a thermoplastic polymeric material,
   wherein the stationary phase outer periphery is between the outer peripheries of the inlet and outlet housing members forms a fluid tight hermetic thermoplastic seal between the outer peripheries of the inlet and outlet housing members formed by heating the outer periphery of the stationary phase.

14. The column of claim 13, wherein the stationary phase comprises:
   (a) a plurality of layers of swellable fibrous matrix; and
   (b) a spacer means having an outer periphery between each layer of swellable fibrous matrix for permitting controlled swelling thereof and enhancing the distribution of sample flowing through the stationary phase, and
   the spacer means comprising a thermoplastic polymeric material in the outer periphery thereof.

15. The column of claim 13, wherein the swellable fibrous matrix is a polysaccharide covalently bonded to a synthetic polymer having the chromatographic functionality, the synthetic polymer being the thermoplastic polymeric material contained in the fibrous matrix.

* * * * *